(12) United States Patent
Dufresne et al.

(10) Patent No.: US 9,533,288 B2
(45) Date of Patent: Jan. 3, 2017

(54) METHOD FOR PREPARING SUPPORTED METAL CATALYSTS FOR HYDROGENATING UNSATURATED HYDROCARBONS

(71) Applicant: EURECAT S.A., La Voulte-sur-Rhône (FR)

(72) Inventors: Pierre Dufresne, Valence (FR); Sharath Kirumakki, Friendswood, TX (US)

(73) Assignee: Eurecat S.A., La Voulte-sur-Rhône (FR)

(*) Notice: Subject to any disclaimer, the term of this patent is extended or adjusted under 35 U.S.C. 154(b) by 260 days.

(21) Appl. No.: 14/082,992

(22) Filed: Nov. 18, 2013

(65) Prior Publication Data
US 2014/0155664 A1    Jun. 5, 2014

Related U.S. Application Data

(60) Provisional application No. 61/734,709, filed on Dec. 7, 2012.

(30) Foreign Application Priority Data

Nov. 30, 2012 (FR) .................... 12 61449

(51) Int. Cl.
| | | |
|---|---|---|
| *B01J 23/89* | (2006.01) | |
| *C07C 5/09* | (2006.01) | |
| *B01J 37/02* | (2006.01) | |
| *B01J 37/34* | (2006.01) | |
| *B01J 23/42* | (2006.01) | |
| *B01J 23/44* | (2006.01) | |
| *B01J 23/755* | (2006.01) | |
| *C10G 45/34* | (2006.01) | |
| *C10G 45/40* | (2006.01) | |
| *C10G 45/36* | (2006.01) | |
| *C10G 45/46* | (2006.01) | |
| *C10G 45/48* | (2006.01) | |
| *C10G 45/52* | (2006.01) | |

(52) U.S. Cl.
CPC ............. *B01J 23/892* (2013.01); *B01J 23/42* (2013.01); *B01J 23/44* (2013.01); *B01J 23/755* (2013.01); *B01J 37/0217* (2013.01); *B01J 37/0225* (2013.01); *B01J 37/0228* (2013.01); *B01J 37/0244* (2013.01); *B01J 37/348* (2013.01); *C07C 5/09* (2013.01); *C10G 45/34* (2013.01); *C10G 45/36* (2013.01); *C10G 45/40* (2013.01); *C10G 45/46* (2013.01); *C10G 45/48* (2013.01); *C10G 45/52* (2013.01); *C10G 2300/1088* (2013.01); *C10G 2300/1096* (2013.01)

(58) Field of Classification Search
CPC ............. C07C 5/08; C07C 5/09; C07C 7/163; C07C 7/167; C07C 11/24; C10G 45/32; C10G 45/34; C10G 45/36; C10G 45/40; B01J 23/40; B01J 23/64; B01J 23/745; B01J 23/755; B01J 23/892; C25D 5/10; C25D 5/12; C25D 5/16; C25D 3/50; C25D 3/52; C25D 3/12
USPC 502/326, 329–331, 337, 339, 324; 585/250, 258–260; 106/1.21, 1.27, 1.28; 205/80, 102, 105, 153, 155, 156, 176, 177, 205/181, 182, 238–240, 242–244, 246–247, 205/255, 257, 264–267, 271, 273
See application file for complete search history.

(56) References Cited

U.S. PATENT DOCUMENTS

| | | | |
|---|---|---|---|
| 3,150,065 A * | 9/1964 | Fatzer ...................... | B21B 1/22 205/125 |
| 3,719,739 A | 3/1973 | Thompson | |
| 3,882,050 A | 5/1975 | Niebylski | |
| 4,377,454 A | 3/1983 | Bommaraju | |
| 4,416,742 A | 11/1983 | Kinase et al. | |
| 4,743,577 A | 5/1988 | Schroeder et al. | |
| 5,318,688 A | 6/1994 | Najjar et al. | |
| 6,676,919 B1 | 1/2004 | Fischer et al. | |
| 2001/0042344 A1 | 11/2001 | Ohmi et al. | |
| 2003/0207761 A1 * | 11/2003 | Ding .................... | B01J 23/892 502/326 |
| 2004/0023798 A1 | 2/2004 | Kaibel | |
| 2005/0113615 A1 * | 5/2005 | Lowe .................... | B01J 23/464 585/259 |
| 2008/0254311 A1 * | 10/2008 | Chen .................... | B32B 15/013 428/613 |
| 2009/0008258 A1 * | 1/2009 | Rei ...................... | B01D 53/944 205/177 |
| 2012/0209042 A1 * | 8/2012 | Mamedov ................ | C07C 5/09 585/275 |

FOREIGN PATENT DOCUMENTS

| | | |
|---|---|---|
| DE | 10049338 | 4/2002 |
| EP | 0739999 A1 | 10/1996 |
| EP | 1052027 A1 | 11/2000 |
| FR | 2763259 A1 | 11/1998 |
| FR | 1261449 | 11/2012 |
| WO | 9640425 | 12/1996 |

* cited by examiner

*Primary Examiner* — Patricia L Hailey
(74) *Attorney, Agent, or Firm* — Saul Ewing LLP; Peter C. Lauro, Esq.

(57) ABSTRACT

The present invention relates to a method for preparing a supported metal catalyst for the selective hydrogenation of unsaturated hydrocarbons, characterized in that it comprises the following steps:
  a) electroplating a layer of nickel on a metallic support, and then
  b) electroplating a top layer of platinum and/or palladium.
The present invention also relates to the supported metal catalyst obtained by this process, and the use thereof in hydrogenation reactions of unsaturated hydrocarbons, in particular for the selective hydrogenation of light olefins.

23 Claims, No Drawings

METHOD FOR PREPARING SUPPORTED METAL CATALYSTS FOR HYDROGENATING UNSATURATED HYDROCARBONS

RELATED APPLICATIONS DATA

This application claims priority to French Patent Application No. 1261449, filed Nov. 30, 2012 and U.S. Provisional Patent Application No. 61/734,709, filed Dec. 7, 2012. The entire disclosures of the aforementioned patent applications are incorporated herein by this reference.

The present invention relates to a method for the preparation of supported catalysts, that is to say solid catalysts whose active phase is at the surface of a solid support.

The present invention relates more specifically to the preparation of metal catalysts that are useful for hydrogenating unsaturated hydrocarbons, and that contain platinum and/or palladium deposited on a support.

The present invention also relates to catalysts obtainable by this process and their use in the reactions of hydrogenation of unsaturated hydrocarbons, and more particularly in the selective hydrogenation of olefinic cuts.

Many industrial processes for transforming organic compounds include one or more stages of hydrogenation, which use catalysts called "hydrogenating catalysts", that are often supported catalysts comprising of one or more "hydrogenating" metals (that is, metals of the platinum group) deposited on an inorganic support.

Such catalysts are for example used in the petroleum or petrochemical industry to hydrogenate unsaturated hydrocarbons such as in particular acetylenic compounds (triple bonds), ethylenic compounds (double bonds), and/or aromatic compounds.

These catalysts must be particularly active, in other words, they must promote the best performance of the desired reaction (s), while being selective, in other words, they must avoid side reactions not desired.

A reaction that is particularly difficult to control is the selective hydrogenation of light olefins.

Light olefins (including alkenes, typically from 2 to 6 carbon atoms), are important raw materials used in the preparation of many polymers and chemicals.

They are most often derived from petroleum refining, including cracking or pyrolysis of heavier cuts. However, the cuts comprising light olefins often contain greater or lesser amounts of acetylene and/or dienes, which are undesirable compounds that compromise the subsequent use of olefins.

These compounds are eliminated from the cuts comprising light olefins by selective hydrogenation reactions. The catalysts employed in these reactions should be highly selective in that they should promote the hydrogenation of acetylene and/or dienes to olefins, without hydrogenating the olefins. They are usually catalysts having an active phase based on palladium that is deposited on an inorganic support of alumina or silica type.

Continuing its research in the field of hydrogenating catalysts, the Applicant has now discovered that catalysts that are particularly active and highly selective could be prepared by electroplating on a metal support specific layers of specific metals.

Thus, the present invention relates to a method for preparing a supported metal catalyst for hydrogenating unsaturated hydrocarbons, characterized in that it comprises the following steps:

a) electroplating a layer of nickel on a metallic support, and then b) electroplating a top layer of platinum and/or palladium.

The process according to the invention allows preparing catalysts for hydrogenating unsaturated hydrocarbons that are highly active and selective. These catalysts are specifically effective for the selective hydrogenation of hydrocarbons, particularly for the selective hydrogenation of light olefins. The specific character of the catalysts of the invention is mainly their selectivity, that is to say their capacity to completely hydrogenate the diolefins and acetylenes (triple bonds) to olefins, without hydrogenating the olefins.

These catalysts also have the advantage of being highly resistant to wear and/or abrasion. Notably, the top layer of platinum and/or palladium adheres particularly well to the catalyst, less metal is removed over time than for some of the prior art catalysts, which ensures a good durability of the catalyst, and holds its level of activity over time very well.

These catalysts also have the advantage of being prepared from supports that can be made of low cost materials, such as materials already used in other applications, such as Raschig rings, Pall rings, packing elements of distillation columns, metallic wires, woven fabrics from metal wires, metal grids.

Another advantage of these catalysts is their ease of recycling at the end of their use. Because of their composition being substantially or totally metallic, the recovery of precious metals is simplified, while the catalysts conventionally employed in the prior art consist of a very small amount of metal deposited on an inorganic support (alumina, silica . . . ), which makes it more difficult for metal recycling.

The catalysts of the invention are prepared from a metal support, that is to say a support composed of a material (possibly composite) containing one or more metals.

For this purpose any material can be employed that contains an amount of metals and/or metal alloys that is sufficient to make the support electrically conductive, in order to allow the electroplating of metal layers on its surface.

Preferably, the support consists of one or more metals selected from iron, chromium, nickel, copper, molybdenum, aluminum, zinc, and alloys of these metals.

More preferably, the support contains at least 50% by weight of iron and/or iron alloy such as in particular steel. According to a preferred embodiment, stainless steel is used. Stainless steel has the advantage of being widely available commercially under various geometric shapes.

However, other specific types of alloys can also be used. For example, mention can be made of Monel, a nickel and copper alloy, which is also suitable for this application. It has however the disadvantage of being less commercially available in desired geometric shapes.

Thus, in a preferred embodiment of the invention, the support is made of stainless steel.

The method of the invention comprises at least two steps a) and b), each consisting in electroplating a layer of metal onto the metallic support.

In a manner known per se, by "electroplating" it is meant a method according to which one or more metal(s) is (are) deposited on the surface of the metallic support from a solution of cations of the metal(s) to be deposited by means of an electric current. This technique is also known in the art under the name of electrodeposition and uses the principle of electrolysis.

For this purpose, the metal support is preferentially dipped into a solution of cations of the metal(s) to be deposited, and forms the cathode of the electrolytic system.

One or more anode(s), for example based on carbon is (are) also immersed (s) in the solution, and the electric current is circulated between the anode(s) and the cathode, until deposition on the cathode (in other words, on the support) of a metal layer having the desired thickness.

The method according to the invention thus comprises a step a) consisting in electroplating a layer of nickel on the metal support.

This step is preferably carried out using an aqueous solution of one or more nickel salts, which can be particularly chosen from nickel chloride ($NiCl_2$), nickel sulfate ($NiSO_4$) and nickel sulfamate $Ni(NH_2SO_3)_2$, and preferably from an aqueous solution of nickel chloride ($NiCl_2$). Particularly preferred is an aqueous solution of nickel chloride ($NiCl_2$) having an acid pH and containing hydrochloric acid (HCl).

The solution may contain other elements, such as for example, boric acid, organic acids, sugars, surfactants, inorganic salts (chlorides, cyanides . . . ).

Step a) is typically carried out at a moderate temperature ranging from 10 to 100° C., preferably from 20 to 90° C. and at atmospheric pressure (760 mm Hg).

According to the invention, the nickel layer is preferably deposited directly onto said metal support, and more preferably completely covers the surface of the support.

The thickness of this layer preferably ranges from 0.01 μm to 10 μm, and more preferably from 0.05 μm to 2 μm.

The method according to the invention also comprises a step b) that consists in electroplating a top layer of platinum and/or palladium.

According to a particularly preferred embodiment of the invention, step b) consists in electroplating a layer comprising palladium, and more preferably step b) consists in electroplating a layer consisting of palladium.

Electroplating in step b) is preferably carried out using an aqueous solution containing platinum and/or palladium, preferably under the form of salt(s) and/or complexe(s).

Such compounds may be chosen from:
The salts and complexes of platinum, including halogenated, amino or amino-nitro salts and complexes of platinum, and in particular: $Pt(NH_3)_2(NO_2)_2$, $Pt(NH_3)_4(NO_2)_2$, $Pt(NH_3)_4Cl_2$;
The salts and complexes of palladium, including halogenated, amino or amino-nitro salts and complexes of palladium, and preferably palladium tetramine and palladium ethylenediamine salts, and in particular $Pd(NH_3)_2(NO_2)_2$, $Pd(NH_3)_4(NO_2)_2$, $Pd(NH_3)_4Cl_2$.

Such compounds are dissolved and a pH preferably greater than 5 is maintained.

More preferably an aqueous solution of one or more salts or complexes of palladium, and particularly preferably an aqueous solution of palladium tetramine salt is used.

Step b) is typically carried out at a moderate temperature ranging from 10 to 100° C., preferably from 30 to 90° C. and at atmospheric pressure.

According to the invention, the layer of platinum and/or palladium is the top layer of the catalyst, that is to say, it constitutes the outer surface of the catalyst. This means in particular that no other compound, in particular no other type of metal is deposited above this layer.

The electroplating is preferably carried out in step b) so as to cover the entire surface of the catalyst, in other words, the layer of platinum and/or palladium extends over the entire outer surface of the catalyst, and thereby fully covers the lower layer(s).

The thickness of this layer preferably ranges from 0.01 to 1 μm and more preferably from 0.02 to 0.1 μm.

Before step a) it may be necessary to perform one or more prior treatments of surface preparation of the support, using techniques known in the art. In particular, any traces of organic residues should preferably be eliminated. To this end a cleaning step using an organic solvent, such as acetone, or an alkali cleaning product, such as sodium hydroxide, may be performed. Techniques such as ultrasonic cleaning can also be used. Then chemical etching, eg using hydrochloric acid, may be advantageous to promote adhesion of the metal layers deposited on the support.

At the end of steps a) and b), the catalyst is preferably washed, for example with water at room temperature. It can also be dried to remove water at temperatures ranging from 20 to 100° C.

The electroplating of one or more metals of the platinum group according to step b) can be performed directly over the nickel layer that has been deposited in step a).

It is also possible to perform, between step a) and step b), one or more intermediate steps, including one or more steps of depositing one or more metallic intermediate layers. Such deposits can also advantageously be performed by electroplating.

Thus, in a preferred embodiment, the method according to the invention comprises, between step a) and step b), an intermediate step e) that consists in electroplating a layer of one or more additional metals that are different from nickel and platinum group metals (platinum, palladium, ruthenium, rhodium, osmium, and iridium).

The additional metal or metals are preferably selected from metals that are catalytically neutral with respect to hydrogenation reactions of hydrocarbons, in particular with respect to hydrogenation reactions of alkenes (having one or more double bonds) and alkynes.

Preferably, this or these additional metal(s) are selected from gold, silver, zinc, manganese and copper.

The deposition of such an intermediate layer of catalytically neutral metal covers the lower layer of nickel that can have a negative influence on the performance and especially the selectivity of the reactions of hydrogenation hydrocarbons.

It becomes thus possible to minimize the amount of platinum and/or palladium constituting the upper layer, that are particularly expensive metals, while maintaining good performance in terms of activity and selectivity of the catalyst even in case the top layer may be of insufficient thickness locally (at certain points of the catalyst) eg due to wear of the catalyst.

According to a particularly preferred embodiment, such additional metal(s) are selected from colored metals, that is so say, metal(s) that have a color different from the color of nickel (silvery white).

Gold or copper, and especially copper, are thus particularly preferred.

The deposition of a colored metal layer presents the advantage of allowing to control in a particularly simple manner, i.e. by visual control, the step b) of depositing the top layer of platinum and/or palladium.

Indeed, it is important to ensure in step b) that the upper layer of platinum and/or palladium completely covers all the surface of the catalyst, in order to ensure optimum efficiency of the catalyst, while using the amount of platinum and/or palladium strictly necessary to achieve this goal, especially as these metals are particularly expensive.

The presence of an intermediate colored metal layer can help to visually monitor the progress of electroplating in step b), and thus to stop it as soon as the colored metal layer is no longer visible, indicating that the catalyst surface is completely coated with platinum and/or palladium. Such visual control is easier to perform than classical methods of thickness measurement which are more complex.

However, it is also possible to monitor the progress of step b) by other methods, such as in particular using electron microscopy. It is also possible to use methods such as X-ray Photoelectron Spectroscopy (XPS)

The intermediate step e) is preferably carried out using an aqueous solution of one or more salts of said additional metal(s). In the case of copper, the deposit is preferably carried out using an aqueous solution of copper salt(s) which can be particularly chosen from copper chloride ($CuCl_2$), copper acetate $(CH_3COO)_2Cu$, copper fluoborate $Cu(BF_4)_2$, copper sulfate ($CuSO_4$), and mixtures thereof.

Step e) can be more preferably be carried out using a dilute solution of copper sulfate ($CuSO_4$) and sulfuric acid.

The solution may contain additional elements, such as for example, boric acid, organic acids, sugars, surfactants, inorganic salts (chlorides, cyanides . . . ).

Step e) is typically carried out at a moderate temperature of between 10 and 100° C., and preferably between 30 and 90° C.

The amount of additional metal deposited during step e) is preferably the minimum amount required to achieve complete coverage of the nickel layer deposited in step a). Obtaining such a complete coverage of the nickel layer can also be controlled visually in the case the additional metal is colored (such as gold or copper), or it can be controlled by methods such as electron microscopy, X-ray photoelectron spectroscopy The thickness of the layer of additional metal that is deposited during step e) preferably ranges from 0.01 to 10 μm, and more preferably from 0.05 to 2 μm.

The invention also concerns the supported metal catalyst, obtainable by the method as described above.

Such a catalyst is preferably under the form of solid particles of small size such as beads, particles having a more or less cylindrical shape or in the form of wires, fabrics, grids or any other suitable form.

The shape of the catalyst depends generally on the original metal support, and it is therefore necessary to use a support having the desired shape for the final catalyst.

The catalyst according to the invention can in particular be used in reactions of hydrogenation of unsaturated hydrocarbons.

It is more preferably used in processes for the selective hydrogenation of light olefins, that is to say for the selective hydrogenation of hydrocarbon cuts containing alkenes and a substantial amount of dienes and/or alkynes having 2 to 12 carbon atoms.

These processes can handle feeds of different types, such as in particular steam cracking gasoline also called pygas ("pyrolisis gasoline"), as well as C4 cuts, C3 cuts or C2 cuts from steam cracking processes.

In a particular embodiment, the catalyst of the invention is used for the selective hydrogenation of a hydrocarbon cut containing acetylene, such as the C2 cut from steam cracking, with the aim of converting acetylene to ethylene in the presence of hydrogen. The catalyst according to the invention allows converting acetylene to ethylene without hydrogenating the latter compound or the other olefins that may be present in the feed.

In such a selective hydrogenation processes, the liquid feed and/or gas is contacted with hydrogen and the catalyst of the invention at a temperature ranging from 30 to 200° C. and at a pressure ranging from 10 to 40 bars ($10^5$ to $4.10^6$ Pa-0.1 to 4 MPa).

In the particular case of hydrogenation of acetylene to ethylene, the conditions are preferably a temperature ranging from 30 to 100° C. and a pressure ranging from 10 to 40 bar ($10^5$ to $4.10^6$ Pa-0.1 to 4 MPa).

During its use, the catalyst according to the invention is likely to deactivate gradually It may however be regenerated in an easy and efficient manner, in particular by carrying out one or more treatments of the catalyst in a reducing medium (hydrogen) or in an oxidizing medium (air) at a temperature above 100° C. and preferably between 200 and 500° C., thereby restoring the activity of a catalyst according to the invention that has been deactivated. The following examples are given by way of illustration of the present invention.

EXAMPLES

Preparation of Catalyst Supports

The catalysts described in the following examples have been prepared on a support consisting of metal packing elements used in distillation column marketed under the name "Pro-Pak protruded Metal Packing Distillation" by Cannon Instrument Company. The size of these elements is 0.16 inch (4.064 mm) and are made of 316 stainless steel.

Preparation of the support is effected by treatment of their surface, in two steps: solvent washing and then acid treatment.

The first step consists in solvent degreasing. This step removes organic deposits on the surface of the support. An amount of 1 g of support is immersed in a beaker containing 20 ml of acetone for 2 minutes while stirring, then removed and dried in a muffle furnace at 100° C. for 5 minutes.

The second step is an acid pickling. It improves the adhesion of metal layers deposited by electroplating.

For this purpose, the degreased support is placed in a beaker of 20 ml of 15% hydrochloric acid (diluted with distilled water) previously heated to 60° C. and left for 3 minutes.

The support is then immediately transferred to the next bath for electroplating, avoiding prolonged exposure to air.

Comparative Example 1

Direct Deposition of Palladium on Steel—Poor Adhesion—No Activity Test

A conventional electroplating setup was used with a DC current system. A catalyst was prepared as follows:

An amount of 1 g of the support prepared as described above is immersed in 200 ml of a solution of palladium tetramine chloride and (2.5 g of Pd per liter) the support constituting the cathode of the system. The anode is a titanium plate covered with platinum. The solution is constantly agitated during the operation. A voltage of 1.6 Volt is applied for 5 minutes at a temperature of 50° C.

The catalyst thus obtained was rinsed with 200 ml of distilled water.

A visual inspection showed that under these conditions the palladium layer is not adherent and a simple rub with a cloth removed the Pd layer partially.

Thus, these conditions are not satisfactory.

Comparative Example 2

Nickel on Steel Catalyst—Poor Activity

The same plating assembly and the same raw material as in Example 1 were used. A catalyst was prepared as follows An amount of 1 g of support was immersed in 200 ml of an acidic solution of nickel chloride, containing 150 g/l of HCl and 50 g/l of nickel (expressed as Ni), at a temperature of 20° C. The support constitutes the electrode, the other electrode being a Nickel bar.

The electroplating was carried out in three distinct phases: first, the application of a voltage of 1 Volt by plugging the support as an anode for 2 minutes, then reversing the electrodes for 3 minutes at 1.9 V, then reversing again for 3 minutes at 1.9 V.

The catalyst thus obtained was rinsed with 200 ml of distilled water.

The catalyst thus obtained was tested on the reaction of selective isoprene hydrogenation.

Example 3 According to the Invention

Catalyst Made of Palladium on Nickel on Steel, Average Content of Palladium The nickel-coated support obtained in Example 2 was subjected to deposition of palladium in the conditions as described in Example 1:

An amount of 1 g of the support was immersed in 200 ml of a solution of palladium tetramine chloride (2.5 g of Pd per liter), and constitutes the cathode of the system. The anode was a titanium plate covered with platinum. A voltage of 1.6 Volt was applied for 2 minutes at a temperature of 50° C.

The catalyst thus obtained was rinsed with 200 ml of distilled water.

The catalyst thus obtained was tested on the reaction of selective isoprene hydrogenation.

Example 4 According to the Invention

Catalyst Made of Palladium on Nickel on Steel, High Content of Palladium

The catalyst of this example was prepared in the same conditions as the previous example, with the difference that the deposition time was doubled (from 2 minutes to 4 minutes), on order to increase the amount of palladium.

The catalyst thus obtained was tested on the reaction of selective isoprene hydrogenation.

Example 5 According to the Invention

Catalyst Made of Palladium on Copper on Nickel on Steel, Low Content Palladium The nickel-coated support obtained in Example 2 was subjected to a copper deposit prior to the deposition of palladium (the latter being produced under the same conditions as in Example 1):

An amount of 1 g of the support obtained in Example 2 was immersed in 200 ml of an acidic solution of copper sulfate, containing 50 g/l of sulfuric acid ($H_2SO_4$) and 50 g/l copper (expressed as Cu), at a temperature of 20° C. This support constituted an electrode, the other being a copper bar. The electroplating was carried out in three distinct phases: first, the application of a voltage of 1.5 V by connecting the support as an anode for 1 minute, then reversing the electrodes for 3 minutes at 1.5 V, then reversing again for 2 minutes at 1.5 V.

The copper-covered, red support thus obtained, was rinsed with 200 ml of distilled water.

An amount of 1 g of this copper coated support was then immersed in 200 ml of a solution of palladium tetramine chloride (2.5 g of Pd per liter), and constituted the cathode of the system. The anode was a titanium plate covered with platinum. A voltage of 1.6 Volt was applied for 2 minutes at a temperature of 50° C.

The catalyst thus obtained was rinsed with 200 ml of distilled water.

The catalyst thus obtained was tested on the reaction of selective isoprene hydrogenation.

Activity Test by Selective Hydrogenation of Isoprene:

Description of the Activity Test Used:

The catalysts prepared as described above were tested in catalytic selective hydrogenation of isoprene (model molecule), in an autoclave under hydrogen pressure. Isoprene is a diolefin which may be hydrogenated first to isopentene (specifically three isomers, 2-methyl-1-butene, 2-methyl-2-butene, 3-methyl-1-butene), and a second time to isopentane.

The weight of catalyst in the autoclave was 0.1 g.

The reactant used was composed of isoprene to 5% by weight, diluted in heptane.

The temperature was 100° C., the hydrogen pressure was maintained at 0.7 MPa.

The test consists in determining the following three values:

T1, which is the time in minutes required for the isoprene concentration to fall to 1% by weight in the reaction medium;

T2 is the time in minutes required for the isopentane concentration to reach 2% by weight in the reaction medium;

Selectivity is the molar ratio (in %) isopentene/(isopentene+isopentane) at point T1, determined when the concentration of isoprene reached 1.0% by weight.

The test was calibrated with a commercial catalyst type E-series of Chevron Phillips (reference).

The first criterion to assess the activity of catalysts for the selective hydrogenation is the operating window, or delta T, which is T2-T1. The higher the Delta T value, the better the catalyst for the selective hydrogenation of alkenes.

The second criterion is the selectivity.

It is important that the catalyst can hydrogenate isoprene as completely as possible before starting to transform isopentenes in isopentane (the latter reaction corresponds to a decrease of yield of desired product).

Results

The test results are summarized in the table below:

| Example | | Catalyst Deposition Technique | T1 (min) | T2 (min) | Delta T (min) | Sélectivity (%) |
|---|---|---|---|---|---|---|
| — | comparative | Reference commercial catalyst | 92 | 130 | 38 | 96 |
| 2 | comparative | Ni on steel | >240 | >240 | — | — |
| 3 | invention | Pd on Ni on steel-average Pd content | 93 | 180 | 87 | 78 |
| 4 | invention | Pd on Ni on steel, high Pd content | 94 | 204 | 114 | 99 |

| Example | Catalyst Deposition Technique | T1 (min) | T2 (min) | Delta T (min) | Sélectivity (%) |
|---|---|---|---|---|---|
| 5 | invention | Pd on Cu on Ni on steel - low Pd content | 73 | 210 | 137 | 100 |

The main criteria for assessing the efficiency of these catalysts for selective hydrogenation is not the activity, but rather the ease of operation, represented by the operating window delta T, and the selectivity.

This test, which is simpler than the real operating conditions, is simulating the activity time T1. The lower the time T1, the more active the catalyst is.

The operating window (in other words, the temperature difference observed between the start of the hydrogenation of alkyne (acetylene) and the start of hydrogenation of the alkene majority component (ethylene)) is simulated by calculating the difference between T1 and T2 obtained on the model diolefin (isoprene). The larger the Delta T (T2-T1) is, the greater will be the catalyst operating range and therefore easier it will be to operate selectively for the production of olefins.

The selectivity allows to directly asses the propensity of the catalyst not to perform complete hydrogenation to alkane at high conversion levels of isoprene.

The results in the table above show that the catalyst of Example 2 (support plated with nickel) is insufficiently active.

The catalysts of Examples 3, 4 and 5 show improved performance compared to the prior art (commercial reference catalyst).

The invention claimed is:

1. A process for selective hydrogenation of hydrocarbon cuts containing alkenes and a substantial amount of dienes and/or alkynes having 2 to 12 carbon atoms, using a supported metal catalyst prepared by a method comprising the steps of:
   a) electroplating a layer of nickel on a metallic support; and
   b) electroplating a top layer of platinum and/or palladium.

2. A process for selective hydrogenation of light olefins using a supported metal catalyst prepared by a method comprising the steps of:
   a) electroplating a layer of nickel on a metallic support; and
   b) electroplating a top layer of platinum and/or palladium.

3. A process for selective hydrogenation of acetylene to ethylene, using a supported metal catalyst prepared by a method comprising the steps of:
   a) electroplating a layer of nickel on a metallic support; and
   b) electroplating a top layer of platinum and/or palladium.

4. The process according to any one of claims 1-3, wherein the support comprises one or more metals selected from the group consisting of iron, chromium, nickel, copper, molybdenum, aluminum, zinc, and alloys thereof.

5. The process according to claim 4, wherein the support comprises at least 50% by weight of iron and/or iron alloy.

6. The process according to claim 5, wherein the support comprises stainless steel.

7. The process according to any one of claims 1-3, wherein step a) is carried out using an aqueous solution of one or more salts selected from the group consisting of nickel chloride ($NiCl_2$), nickel sulfate ($NiSO_4$) and nickel sulfamate $Ni(NH_2SO_3)_2$.

8. The process according to claim 7, wherein step a) is carried out using an aqueous solution of nickel chloride ($NiCl_2$).

9. The process according to any one of claims 1-3, wherein the thickness of the nickel layer ranges from 0.01 to 10 µm.

10. The process according to claim 9, wherein the thickness of the nickel layer ranges from 0.05 to 2 µm.

11. The process according to any one of claims 1-3, wherein step b) is carried out using an aqueous solution containing a metal selected from the group consisting of platinum, palladium, salts thereof, complexes thereof and mixtures thereof.

12. The process according to claim 11, wherein step b) is carried out using an aqueous solution comprising salt(s) and/or complex(es) of platinum and/or palladium selected from the group consisting of halogenated, amino or amino-nitro salts and complexes of platinum, and halogenated, amino or amino-nitro salts and complexes of palladium.

13. The process according to claim 12, wherein step b) is carried out using an aqueous solution comprising salt(s) and/or complex(es) of platinum selected from the group consisting of halogenated, amino or amino-nitro salts and complexes of platinum selected from the group consisting of $Pt(NH_3)_2(NO_2)_2$, $Pt(NH_3)_4(NO_2)_2$ and $Pt(NH_3)_4Cl_2$.

14. The process according to claim 12, wherein step b) is carried out using an aqueous solution comprising salt(s) and/or complex(es) of palladium selected from the group consisting of palladium tetramine and palladium ethylenediamine salts.

15. The process according to claim 14, wherein the salts and/or complexes of palladium are selected from the group consisting of $Pd(NH_3)_2(NO_2)_2$, $Pd(NH_3)_4(NO_2)_2$ and $Pd(NH_3)_4Cl_2$.

16. The process according to any one of claims 1-3, wherein step b) comprises electroplating a layer of palladium.

17. The process according to any one of claims 1-3, wherein the thickness of the layer of platinum and/or palladium ranges from 0.01 to 1 µm.

18. The process according to claim 17, wherein the thickness of the layer of platinum and/or palladium ranges from 0.02 to 0.1 µm.

19. The process according to any one of claims 1-3, wherein the electroplating of platinum and/or palladium according to step b) is performed directly on top of the nickel layer deposited in step a).

20. The process according to any one of claims 1-3, further comprising, between step a) and step b), an intermediate step e) comprising electroplating a layer of one or more additional metal(s) that is (are) different from nickel and platinum group metals.

21. The process according to claim 20, wherein intermediate step e) comprises electroplating a layer of one or more additional metal(s) selected from the group consisting of gold, silver, zinc, manganese and copper.

22. The process according to claim 21, wherein said one or more additional metal(s) is selected from the group consisting of gold and copper.

23. The process according to claim 22, wherein said additional metal is copper.

* * * * *